(12) United States Patent
Duffy et al.

(10) Patent No.: US 8,343,181 B2
(45) Date of Patent: Jan. 1, 2013

(54) METHOD AND APPARATUS FOR TREATING STENOSES AT BIFURCATED REGIONS

(75) Inventors: Niall Duffy, Tuam (IE); Noreen Moloney, Moycullen (IE); Terry Guinan, Loughrea (IE)

(73) Assignee: Medtronic Vascular, Inc., Santa Rosa, CA (US)

( * ) Notice: Subject to any disclaimer, the term of this patent is extended or adjusted under 35 U.S.C. 154(b) by 1723 days.

(21) Appl. No.: 11/680,834

(22) Filed: Mar. 1, 2007

(65) Prior Publication Data

US 2008/0215018 A1    Sep. 4, 2008

(51) Int. Cl.
*A61M 29/00* (2006.01)

(52) U.S. Cl. .......................................... 606/194
(58) Field of Classification Search .................. 623/1.11, 623/1.35, 1.27, 1.12; 606/191–194, 195; 604/509
See application file for complete search history.

(56) References Cited

U.S. PATENT DOCUMENTS

| | | | |
|---|---|---|---|
| 4,994,071 A | 2/1991 | MacGregor | |
| 5,669,924 A | 9/1997 | Shaknovich | |
| 5,718,724 A | 2/1998 | Goicoechea et al. | |
| 5,720,735 A | 2/1998 | Dorros | |
| 5,723,004 A | 3/1998 | Dereume et al. | |
| 5,749,825 A | 5/1998 | Fischell et al. | |
| 6,071,285 A | 6/2000 | Lashinski et al. | |
| 6,129,738 A | 10/2000 | Lashinski et al. | |
| 2003/0093109 A1 | 5/2003 | Mauch | |
| 2004/0098114 A1 | 5/2004 | Wilson et al. | |
| 2004/0143286 A1* | 7/2004 | Johnson et al. | 606/194 |
| 2005/0102019 A1* | 5/2005 | Yadin | 623/1.11 |

FOREIGN PATENT DOCUMENTS

| | | |
|---|---|---|
| EP | 0804907 A2 | 5/1997 |
| WO | WO01/41677 | 6/2001 |
| WO | WO2005/025458 | 3/2005 |
| WO | WO2005/094728 | 10/2005 |

* cited by examiner

*Primary Examiner* — Thomas McEvoy

(57) ABSTRACT

A bifurcated catheter includes a first catheter branch having a first distal portion and a second catheter branch having a second distal portion. The first and second distal portions are releasably linked together for delivery to a bifurcated region of a body vessel. Upon delivery to the bifurcated region, the first and second distal portions are released from each other such that the first and second catheter branches may be tracked into first and second vessel branches, respectively.

3 Claims, 15 Drawing Sheets

METHOD AND APPARATUS FOR TREATING STENOSES AT BIFURCATED REGIONS

FIELD OF THE INVENTION

The invention relates generally to dilatation catheters, stents and grafts for dilating strictures or stenoses in the human body. More particularly, the invention relates to a balloon catheter, including a delivery system for a bifurcated endoluminal prosthesis, for treating site or sites at or near a bifurcation of a body lumen.

BACKGROUND OF THE INVENTION

The use of balloon catheters with or without stents to treat strictures, stenoses, or narrowings in various parts of the human body is well known in the prior art. Devices of numerous designs have been utilized for angioplasty, stents and grafts or combination stent/grafts. Varied catheter designs have been developed for the dilatation of stenoses and to deliver prostheses to treatment sites within the body lumen.

Devices developed specifically to address the problems that arise in the treatment of stenoses at or near the site of a bifurcation of a body lumen are known in the art. Examples of catheters for use in treating bifurcated lumens or delivery systems for bifurcated endoluminal prostheses are shown in U.S. Pat. No. 5,720,735 to Dorros, U.S. Pat. No. 5,669,924 to Shaknovich, U.S. Pat. No. 5,749,825 to Fischell, et al., and U.S. Pat. No. 5,718,724 to Goicoechea et al.

Various techniques have been used to deliver multiple prostheses in order to provide radial support to both a main blood vessel, for example, and contemporaneously to side branches of the blood vessel. Further, single bifurcated stents and grafts have been developed in order to treat such conditions at the site of a branch of a body lumen. A bifurcated stent and/or graft typically comprises a tubular body or trunk and two tubular legs. Examples of bifurcated stents are shown in U.S. Pat. No. 5,723,004 to Dereume et al., U.S. Pat. No. 4,994,071 to MacGregor, and European Pat. Application EP 0 804 907 A2 to Richter, et al.

Illustrative procedures involving balloon catheters include percutaneous transluminal angioplasty (PTA) and percutaneous transluminal coronary angioplasty (PTCA), which may be used to reduce arterial build-up such as caused by the accumulation of atherosclerotic plaque. These procedures involve passing a balloon catheter over a guide wire to a stenosis with the aid of a guide catheter. The guide wire extends from a remote incision to the site of the stenosis, and typically across the lesion. The balloon catheter is passed over the guide wire, and ultimately positioned across the lesion.

Once the balloon catheter is positioned appropriately across the lesion, (e.g., under fluoroscopic guidance), the balloon is inflated, which breaks the plaque of the stenosis and causes the arterial cross section to increase. Then the balloon is deflated and withdrawn over the guide wire into the guide catheter, and from the body of the patient.

In many cases, a stent or other prosthesis must be implanted to provide permanent support for the artery. When such a device is to be implanted, a balloon catheter which carries a stent on its balloon is deployed at the site of the stenosis. The balloon and accompanying prosthesis are positioned at the location of the stenosis, and the balloon is inflated to circumferentially expand and thereby implant the prosthesis. Thereafter, the balloon is deflated and the catheter and the guide wire are withdrawn from the patient.

Administering PTCA and/or implanting a stent at a bifurcation in a body lumen poses further challenges for the effective treatment of stenoses in the lumen. For example, dilating a vessel at a bifurcation may cause narrowing of an adjacent branch of the vessel. In response to such a challenge, attempts to simultaneously dilate both branches of the bifurcated vessel have been pursued. These attempts include deploying more than one balloon, more than one prosthesis, a bifurcated prosthesis, or some combination of the foregoing.

However, simultaneously deploying multiple and/or bifurcated balloons with or without endoluminal prostheses, hereinafter individually and collectively referred to as a bifurcated assembly, requires highly accurate placement of the assembly. Specifically, deploying a bifurcated assembly requires positioning a main body of the assembly within the trunk of the vessel adjacent the bifurcation, and then positioning the independent legs of the assembly into separately branching legs of the body lumen.

Tracking a bifurcated assembly to a treatment site also presents additional challenges to the more standard PTCA procedure. For example, a bifurcated catheter must be tracked to the site as a unitary device until it reaches the bifurcation. Once it reaches the bifurcated treatment site, it must be positioned within the separate branches of the vessel. Therefore, it must be a unitary device during tracking and be a bifurcated device for treatment.

In order to achieve the foregoing objectives, two guide wires are typically required, one for placement of the assembly into each branch of the bifurcated vessel. Devices known in the prior art fail to track and position a device requiring two guide wires in an expeditious fashion by failing to prevent the entanglement of the wires or other complications which would prevent proper placement of the assembly and/or a smooth withdrawal the catheter and of the guide wires.

Further, devices known in the prior art fail to provide a bifurcated assembly, the distal portion of which functions as a unitary device during tracking and as a bifurcated device for positioning and deployment.

In view of the foregoing, it is an object of this invention to provide improved catheters and methods for use with multiple guide wires for delivering balloon catheters and prostheses designed to treat stenoses at or near a bifurcation of a body lumen.

BRIEF SUMMARY OF THE INVENTION

The present disclosure relates to bifurcated catheters which can be linked together such that they can be tracked to a bifurcated region of a body lumen over a single guide wire. A bifurcated catheter according to the present disclosure includes a first catheter branch having a first distal portion and a second catheter branch having a second distal portion. The first and second distal portions are linked together for delivery to the bifurcated region. Upon delivery to the bifurcated region, the first and second distal portions are released from each other such that the first and second catheter branches may be tracked into first and second vessel branches, respectively.

In an embodiment, the first and second distal portions may be linked together by an appendage disposed on the first distal portion. The appendage is directed towards the second catheter branch and is sized and shaped such that the appendage fits snugly within a distal opening of the second distal portion. Upon delivery of the catheter to the bifurcated region, the appendage is dislodged from the distal opening by pushing against it with a guide wire tracked through the second catheter branch or by pressure from a fluid, such as a saline solution.

In another embodiment, the first and second distal portions may be linked together by a cup disposed on the first distal portion, wherein the cup is sized and shaped to snugly receive the second distal portion. The second distal portion is inserted into the cup. A light adhesive may be added to keep the second distal portion attached to the cup during delivery to the bifurcated region. Upon delivery of the catheter to the bifurcated region, the second distal portion is dislodged from the cup by pushing against the cup with a guide wire tracked through the second catheter branch or by pressure from a fluid, such as a saline solution.

In another embodiment, the first and second distal portions are linked together by a moving pocket disposed on the first distal portion. The moving pocket includes a first portion disposed around and slidable relative to the first distal portion and a pocket portion sized and shaped to snugly receive the second distal portion. The first portion of the moving pocket may be cylindrical with proximal and distal opening such that it can slide along the first distal portion. The pocket portion is coupled to the first portion and may be a closed cylinder with a proximal opening and a distal wall. The second distal portion is inserted into the pocket portion of the moving pocket. Upon delivery of the catheter to the bifurcated region, the second distal portion is dislodged from the pocket by pushing against the distal wall of the pocket portion with a guide wire tracked through the second catheter branch or by pressure from a fluid, such as a saline solution. The moving pocket may slide along a reduced neck portion of the first distal portion, wherein the proximal and distal ends of the reduced neck portion limit the proximal and distal movement of the moving pocket. In another embodiment, proximal and distal stops are provided on the first distal portion to limit the proximal and distal movement of the moving pocket.

In another embodiment, the first and second distal portions may be linked together by a sheath coupled to the first distal portion and wrapped around the second distal portion. The sheath links the first and second distal portions together for delivery to the bifurcated region over a first guide wire. A second guide wire is then advanced into the second branch vessel and the first and second branch catheters are advanced into the first and second branch vessels over the respective first and second guide wires. As the distal portions of the first and second catheter branches separate, the sheath unwinds from the second distal portion. Upon sufficient separation, the sheath completely unwinds from the second distal portion and wraps only around the first distal portion, thereby freeing the first and second catheter branches from each other.

Further features of the invention, its nature and various advantages, will be more apparent from the accompanying drawings and the following detailed description of the preferred embodiments.

BRIEF DESCRIPTION OF DRAWINGS

The foregoing and other features and advantages of the invention will be apparent from the following description of the invention as illustrated in the accompanying drawings. The accompanying drawings, which are incorporated herein and form a part of the specification, further serve to explain the principles of the invention and to enable a person skilled in the pertinent art to make and use the invention. The drawings are not to scale.

DETAILED DESCRIPTION OF THE INVENTION

Specific embodiments of the present disclosure are now described with reference to the figures, wherein like reference numbers indicate identical or functionally similar elements. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician.

Figure 1:
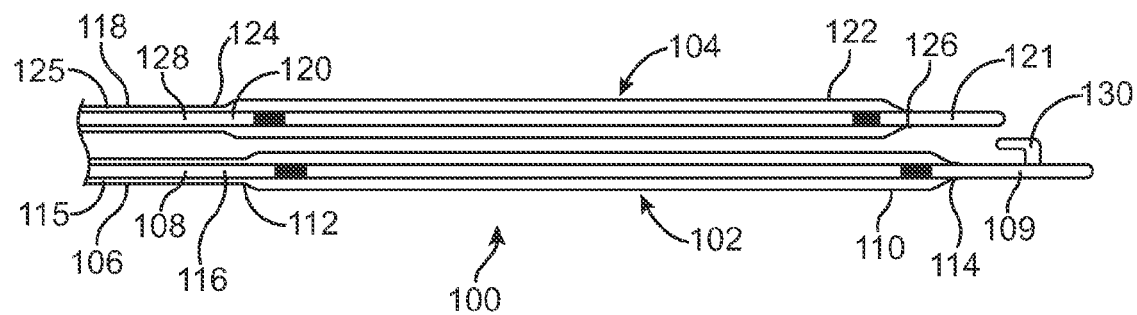
FIG. 1 is a simplified, partial, elevational view of a bifurcated catheter in accordance with an embodiment of the present invention.

An illustrative embodiment of a catheter 100 constructed in accordance with this invention is shown in FIG. 1. The proximal portion of catheter 100 is toward the left in FIG. 1, and the distal portion is toward the right. Catheter 100 may comprise two separate tubular structures linked at particular points along their lengths, or it may consist of a single tubular structure with multiple lumens in its interior.

FIG. 1 depicts a catheter having two branches and two balloons, but more than two balloons may be utilized with the present invention. Alternatively, a bifurcated balloon, either alone or in combination with one or more standard balloons may be utilized.

Catheter 100 includes a first catheter branch 102 and a second catheter branch 104. First catheter branch 102 includes a first outer shaft 106, a first inner shaft 108, and a first balloon 110. A proximal end of first balloon 110 is mounted to a distal portion of first outer shaft 106 at a first proximal junction 112. A distal end of first balloon 110 is mounted to a distal portion of first inner shaft 108 at a first distal junction 114. A first inflation lumen 115 extends between first outer shaft 106 and first inner shaft 108, and is in communication with an interior of first balloon 110. A first guide wire lumen 116 extends through first inner shaft 108.

Similarly, second catheter branch 104 includes a second outer shaft 118, a second inner shaft 120, and a second balloon 122. A proximal end of second balloon 122 is mounted to a distal portion of second outer shaft 118 at a second proximal junction 124. A distal end of second balloon 122 is mounted to a distal portion of second inner shaft 120 at a second distal junction 126. A second inflation lumen 125 extends between second outer shaft 118 and second inner shaft 120, and is in communication with an interior of second balloon 122. A first guide wire lumen 128 extends through second inner shaft 120.

First and second inflation lumens 115, 125 can be conventional, and extend from a proximal portion of catheter 100 outside the patient, which is not pictured. First and second inflation lumens 115, 125 are in fluid communication with the interiors of first balloon 110 and second balloon 122. Thus, first and second inflation lumens 115, 125 are used to supply pressurized inflation fluid to first balloon 110 and second balloon 122 when it is desired to inflate the balloons. Inflation lumens 115, 125 are also used to drain inflation fluid from first balloon 110 and second balloon 122 when it is desired to deflate the balloons.

Although first and second guide wire lumens 116, 128 are shown passing through the interior of first and second balloons 110, 122, they need not. For example, the lumens may be affixed to the exterior of the balloon, or the balloon may be formed with a plurality of folds through which the guide wire passes. Alternatively, the guide wire may pass through the folds of the balloon, as illustrated in U.S. Pat. No. 6,071,285 for a Rapid Exchange Folded Balloon Catheter and Stent Delivery System, the entirety of which is incorporated by reference herein. First and second guide wire lumens 116, 128 are distinct from first and second inflation lumens 115, 125 and are not in fluid communication with the interior of first and second balloons 110, 122. Further, first and second guide wire lumens 116, 128 can begin and terminate generally at any point along first and second catheter branches 102, 104, but preferably they extend distally of first and second balloons 110, 122, respectively.

First catheter branch 104 further includes an appendage or tail 130 coupled to a distal portion 109 of second inner shaft 108. Appendage or tail 130 extends toward a distal tip portion 121 of second inner shaft 120. In the embodiment shown in FIGS. 1-8, appendage or tail 130 includes a first portion 132 extending substantially perpendicular to a longitudinal axis of first branch catheter 102 and towards second branch catheter 104. Appendage or tail 130 further includes a second portion 134 extending proximally substantially parallel to the longitudinal axis of first branch catheter 102. Thus, first and second portions 132, 134 of appendage or tail 130 form a substantially right angle, although it would be understood by one of ordinary skill in the art that various shapes and configurations for appendage 130 are possible. Second portion 134 of appendage 130 is sized and shaped to fit within a distal opening 136 of second inner shaft 120, as shown in detail in FIG. 2. By inserting appendage 130 into second inner shaft 120, first catheter branch 102 and second catheter branch 104 are coupled together for delivery to the site of a lesion. Once at the lesion site, a force delivered from inside of second inner shaft 120 dislodges appendage 130 from second inner shaft 120, thereby freeing second catheter branch 104 from first catheter branch 102, as shown in FIG. 3. The force delivered to dislodge appendage 130 may be a force from a guide wire disposed within second guide wire lumen 128 or a force from a fluid injected in second guide wire lumen 128, for example, a saline solution.

Appendage 130 may be made from a relatively soft material, such as PEBAX® 6333 polyethylene block amide copolymer by Arkema, Inc. of Philadelphia, Pa. Appendage 130 may made from a material that is softer than the main portions of first catheter branch 102, although it may be made from the same material as distal portion 109 of first inner shaft 108 as distal portions of inner shafts are generally made from a relatively soft material. Further, by describing appendage 130 as coupled to distal portion 109 of first inner shaft 108, one of ordinary skill in the art would understand that appendage 130 may be made unitary with distal portion 109.

Figure 4:
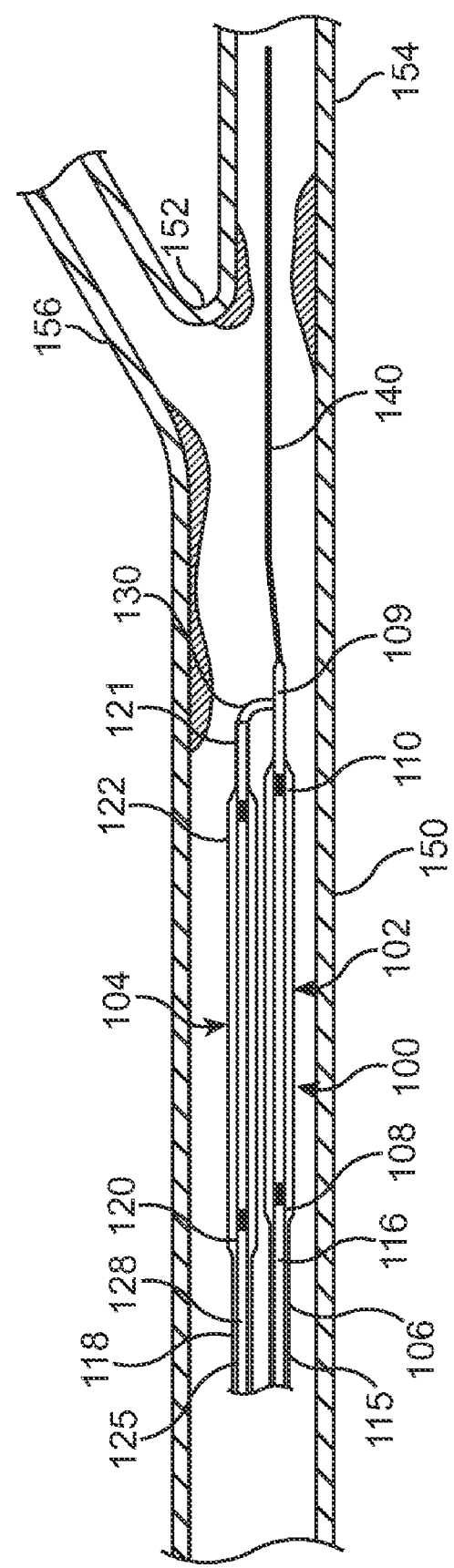
FIG. 4 illustrates the catheter of FIG. 1 in vivo, following the step of threading the catheter over a first guide wire.

With reference to FIGS. 4-8, the manner of practicing the invention will now be discussed. First catheter branch 102 is threaded over a first guide wire 140 which is already in place in the body lumen. More specifically, a proximal end of first guide wire 140 is threaded into a distal opening 138 of distal portion 109 of first inner shaft 108, and through first guide wire lumen 116. First catheter branch 102 is threaded over first guide wire 140 while appendage 130 is inserted into distal portion 121 of second inner shaft 120, thereby coupling the distal portions of first and second catheter branches 102, 104 together, as shown in FIG. 4.

Figure 5:
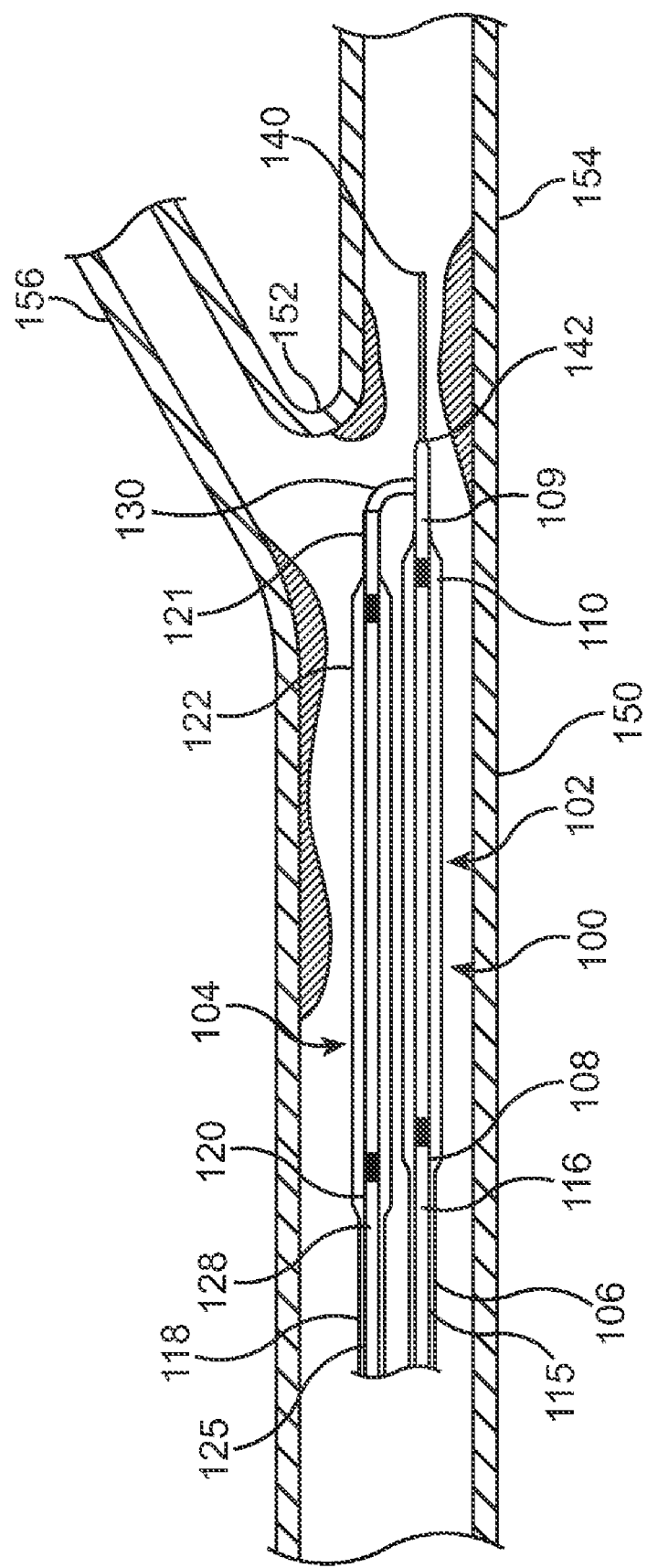
FIG. 5 illustrates the catheter of FIG. 1 in vivo when the catheter has been delivered to the bifurcation site.

Catheter 100 is thus threaded over first guide wire 140 and tracked to a position at or near a bifurcation 152 of a vessel 150, as depicted in FIG. 5. A second guide wire 142 may be pre-installed through second guide wire lumen 128 such that second guide wire 142 is advanced with catheter 100 as catheter 100 is advanced to the bifurcation site 152. Alternatively, second guide wire 142 may be inserted in second guide wire lumen 128 after catheter 100 has reached the bifurcation site 152.

Figure 6:
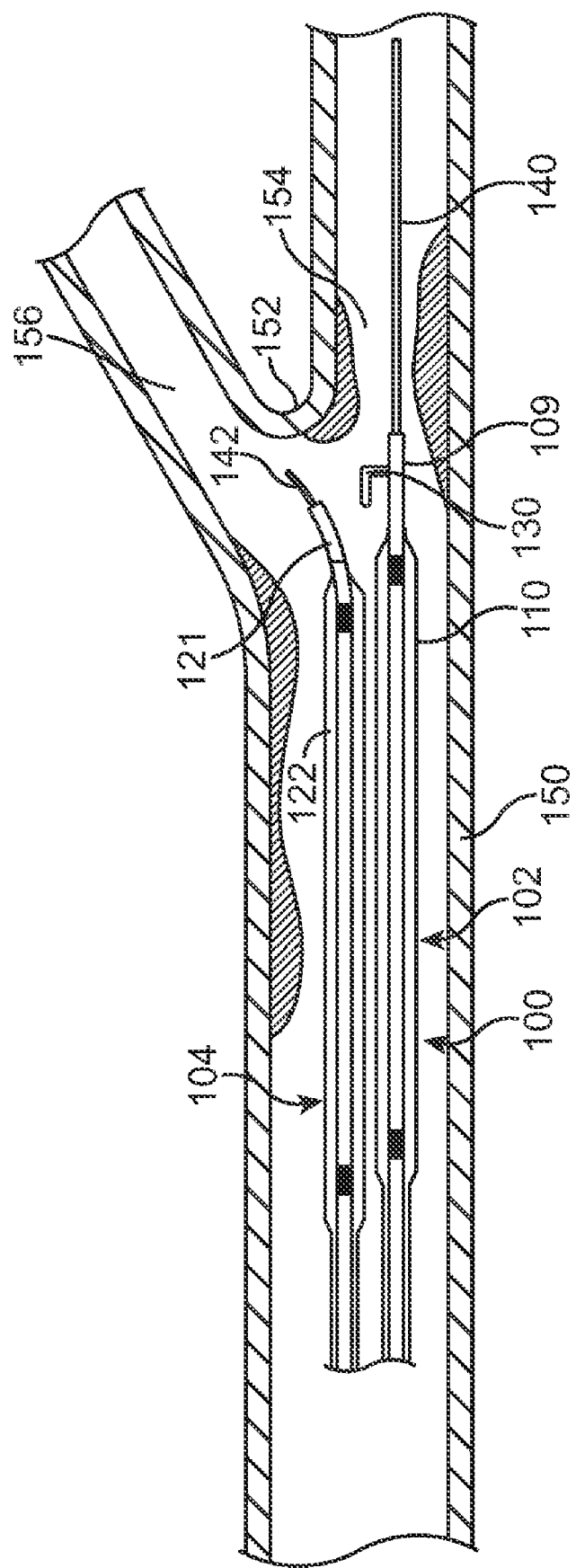
FIG. 6 illustrates the catheter of FIG. 1 after the appendage has been removed from the distal portion of the second catheter branch.

With catheter 100 positioned near bifurcation 152, appendage 130 is removed from distal portion 121 of second inner shaft 120, as shown in FIG. 6. As noted above, appendage 130 may be dislodged from distal portion 121 of second inner shaft 120 by injecting a solution such as saline through second guide wire lumen 128 or by pushing second guide wire 142 against appendage 130 to forced it out of distal portion 121, or by other means as would be apparent to those of ordinary skill in the art.

With catheter 100 positioned near bifurcation 152 and appendage 130 dislodged from distal portion 121 of second inner shaft 120, first and second branches 102, 104 can then be positioned independently of one another such that first and second balloons 110, 122 may be positioned independently of each other. As shown in FIG. 6, second guide wire 142 is extended through distal opening 136 of distal portion 121 of second inner shaft 120. Second guide wire 142 is then extended into a second branch 156 of vessel 150. First guide wire 140 may also be further extended in a first branch 154 of vessel 150, if necessary.

Figure 7:
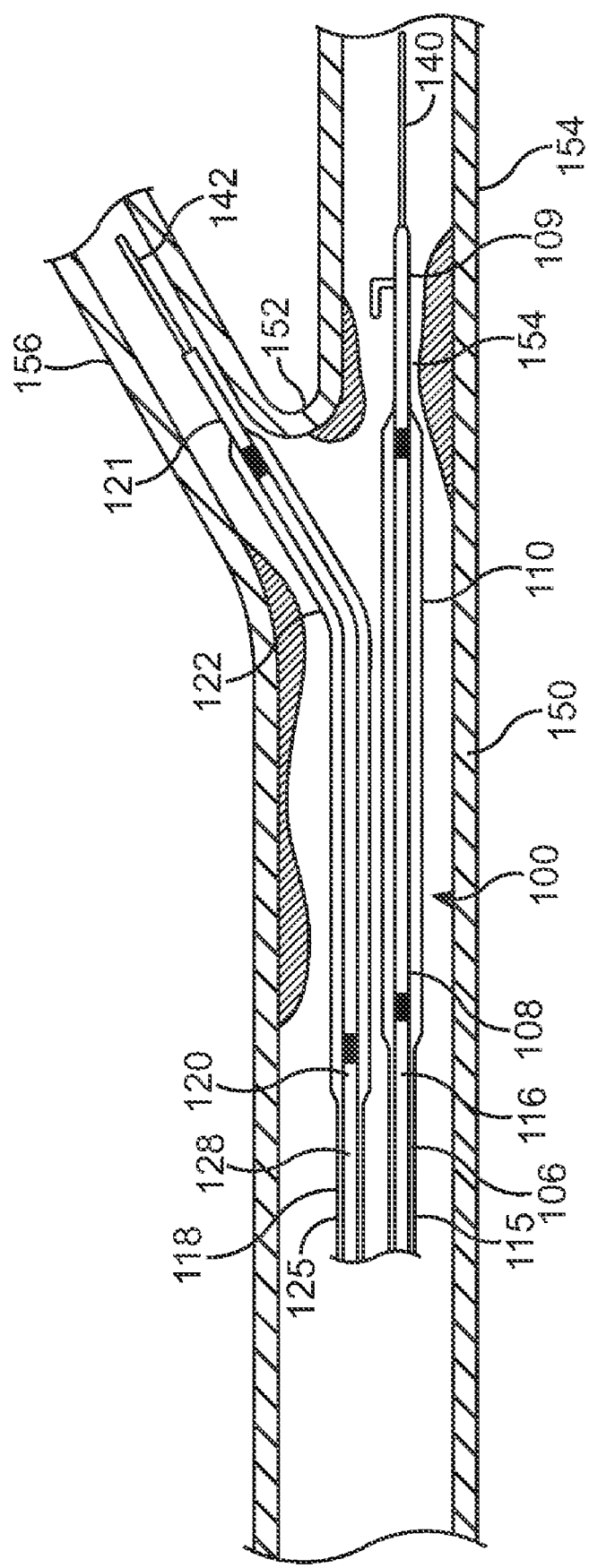
FIG. 7 illustrates the catheter FIG. 1 after the catheter branches have been advanced into the respective vessel branches.

With first guide wire 140 positioned within first branch 154 of vessel 150 and second guide wire 142 positioned within second branch 156 of vessel 150, catheter 100 may be further advanced such that first catheter branch 102 is disposed within first branch vessel 154 and second catheter branch is disposed within second branch vessel 156, as depicted in FIG. 7.

Figure 8:
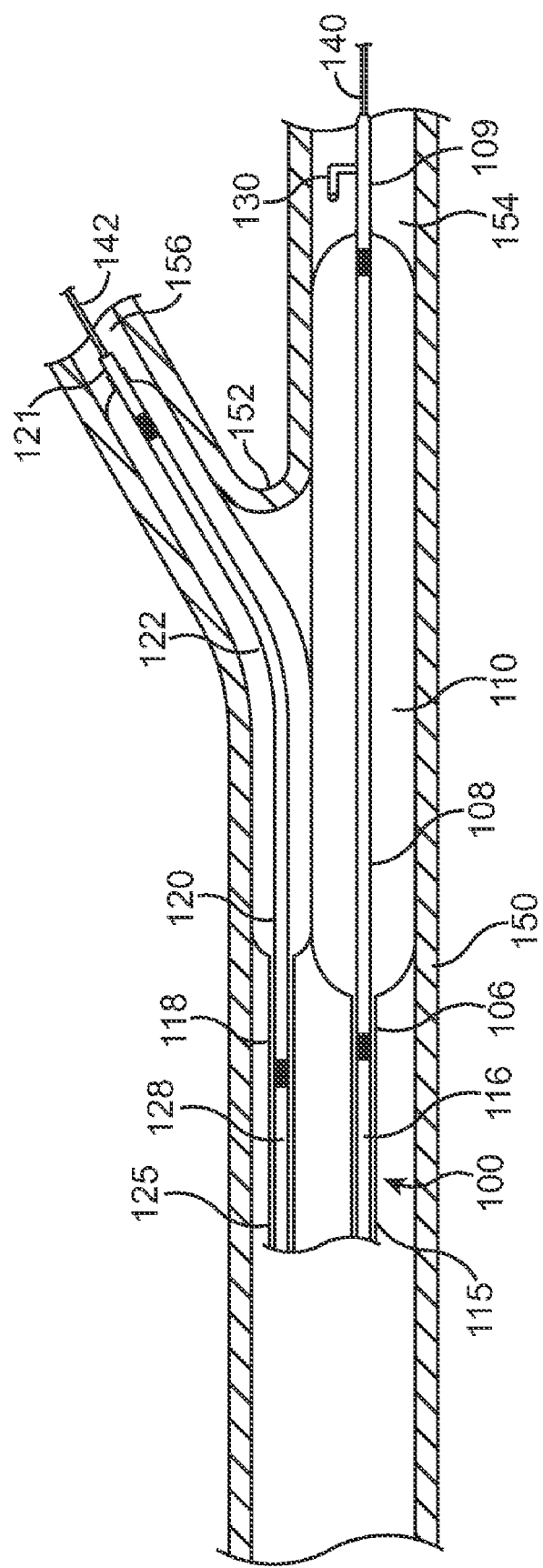
FIG. 8 illustrates the catheter of FIG. 1 subsequent to inflation of the balloon(s).

Once the entire assembly is properly positioned, pressurized fluid is supplied to first and second balloons 110, 122 through first and second inflation lumens 115, 125, as shown in FIG. 8. After first balloon 110 and second balloon 122 have been inflated as described above, first balloon 110 and second balloon 122 are deflated by draining the inflation fluid via first and second inflation lumens 115, 125. This allows the balloons to collapse in preparation for withdrawal of the assembly from vessel 150.

Figure 2:
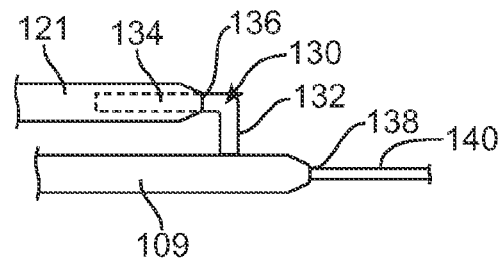
FIG. 2 illustrates a partial, elevational view of the distal portion of the catheter of FIG. 1.
Figure 3:
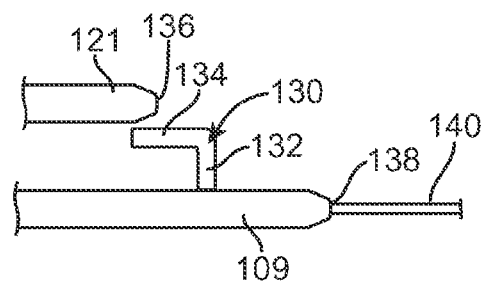
FIG. 3 illustrates a partial, elevational view of the distal portion of the catheter of FIG. 1.

As would be understood by those of ordinary skill in the art, a bifurcated stent may be mounted on first and second balloons 110, 122 of catheter 100, as shown in FIGS. 2-2F of U.S. Pat. No. 6,129,738, the entirety of which is incorporated by reference herein. As noted in the '738 patent, a single bifurcated stent or multiple stents, in place of or in combination with a bifurcated stent, may be deployed utilizing a bifurcated catheter of the present invention.

Figure 9:
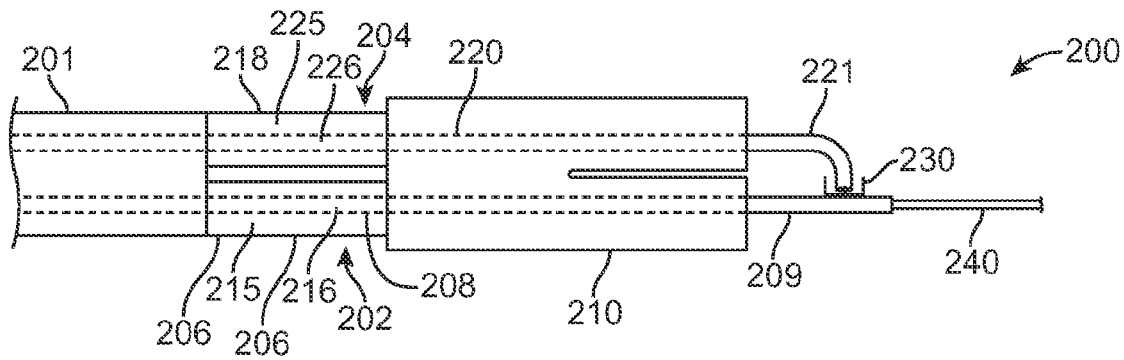
FIG. 9 illustrates a simplified, partial, elevational view of a bifurcated catheter in accordance with another embodiment of the present invention.
Figure 10:
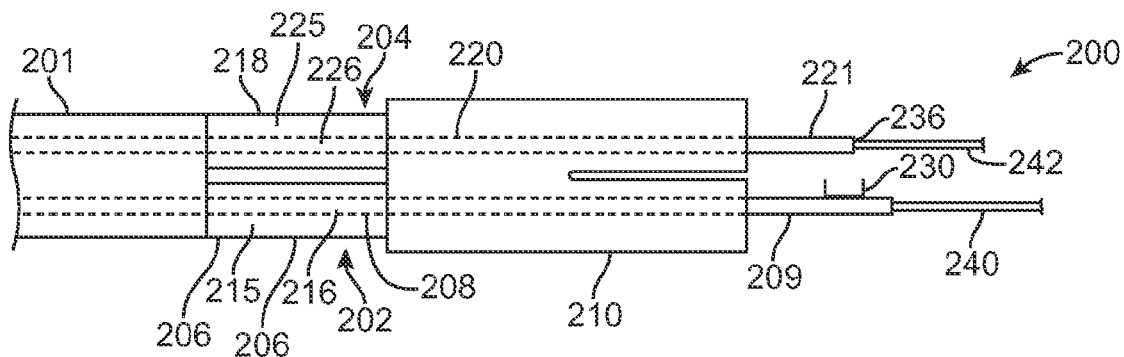
FIG. 10 illustrates the catheter of FIG. 10 with the second catheter dislodged from the cup.

FIGS. 9 and 10 depict another embodiment of a catheter 200 in accordance with the present invention. Catheter 200 includes a proximal portion 201, a first catheter branch 202, and a second catheter branch 204. A bifurcated balloon 210 is mounted on first and second catheter branches 202, 204. As would be apparent to one of ordinary skill in the art, multiple balloons, such as those shown in FIG. 1, may be used instead of a single bifurcated balloon. Similar to catheter 100, first catheter branch 202 includes a first outer shaft 206 and a first inner shaft 208. A first inflation lumen 215 extends between first outer shaft 206 and first inner shaft 208, and is in communication with an interior of bifurcated balloon 110. A first guide wire lumen 216 extends through first inner shaft 208. A second catheter branch 204 includes a second outer shaft 218 and a second inner shaft 220. A second inflation lumen 225 extends between second outer shaft 218 and second inner shaft 220, and is in communication with an interior of bifurcated balloon 210. A second guide wire lumen extends through second inner shaft 220.

Instead of the appendage 130 of catheter 100 of the embodiment of FIGS. 1-8, catheter 200 includes a cup 230 attached to a distal portion 209 of first inner shaft 208. Cup 230 generally faces towards second catheter branch 204 and is sized to snugly fit a distal portion 221 of second inner shaft 220 therein, as shown in FIG. 9. A light adhesive may be added to couple distal portion 221 to cup 230 during delivery of catheter 200 to the bifurcation site. Catheter 200 is delivered through the vasculature to the bifurcation site with distal portion 221 of second inner shaft 220 coupled to cup 230. Thus, distal portions of first catheter branch 202 and second catheter branch 204 are coupled to each other. A first guide wire 240 is disposed within the vessel near the bifurcation, such as in FIG. 4. A proximal end of first guide wire 240 is inserted into a distal end of first guide wire lumen 216 and catheter 200 is advanced along first guide wire to the bifurcation, as described with respect to FIGS. 4 and 5.

Upon reaching the bifurcation, distal portion 221 of second inner shaft 220 is released from cup 230. This release can be accomplished by pushing a second guide wire 242 that is advanced through the second guide wire lumen, out of distal opening 236 of distal portion 221 to push against cup 230. Alternatively, a solution such as saline may be injected through the second guide wire lumen to force distal portion 221 of second inner shaft 220 out of cup 230. The distal portions of first and second catheter branches 202, 204 are thereby released from each other so that they can move independently, as described above with respect to FIG. 6.

With catheter 200 positioned near the bifurcation and distal portion 221 of second inner shaft 220 dislodged from cup 230, first and second branches 202, 204 can then be positioned independently of one another. As described with respect to the above embodiment and FIG. 6, second guide wire 242 is extended through distal opening 236 of distal portion 221 of second inner shaft 220. Second guide wire 242 is then extended into the second branch of the bifurcated vessel and first guide wire 240 may also be further extended into the first branch of the bifurcated vessel, if necessary. With first guide wire 240 positioned within first branch and second guide wire 242 positioned within the second branch, catheter 200 may be further advanced such that first catheter branch 202 is disposed within first branch vessel and second catheter branch is disposed within second branch vessel, as described with respect to the above embodiment and FIG. 7.

Once the entire assembly is properly positioned, pressurized fluid is supplied to bifurcated balloon 210 through first and second inflation lumens 215, 225, as described above with respect to FIG. 8. After bifurcated balloon 210 has been inflated as described above, bifurcated balloon 210 is deflated by draining the inflation fluid via first and second inflation lumens 215, 225. This allows the balloons to collapse in preparation for withdrawal of the assembly from the vessel.

Figure 11:
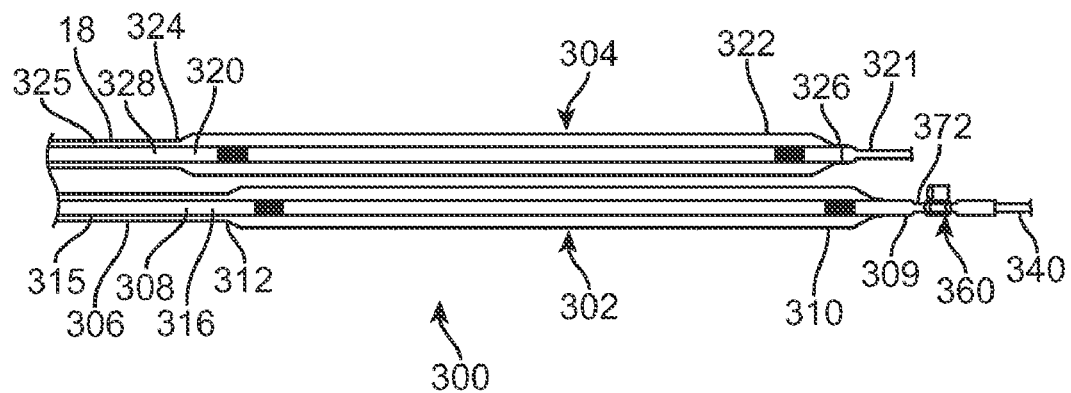
FIG. 11 illustrates a simplified, partial, elevational view of a bifurcated catheter in accordance with another embodiment of the present invention.
Figure 12:
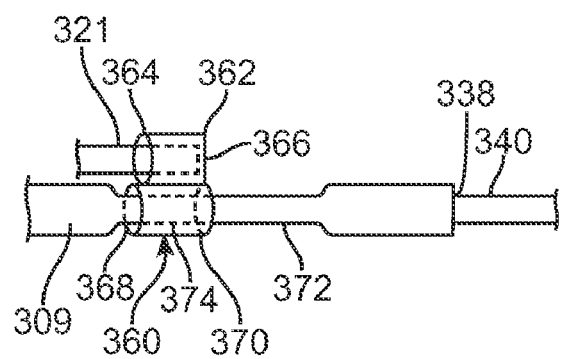
FIG. 12 illustrates a simplified, partial, elevational view of the distal portion of the catheter of FIG. 11, with the distal portions of the catheter branches coupled together.
Figure 13:
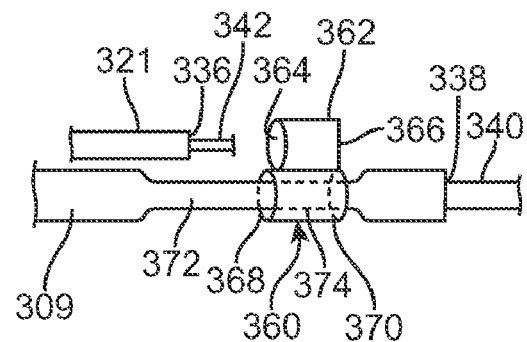
FIG. 13 illustrates a simplified, partial, elevational view of the distal portion of the catheter of FIG. 11, with the distal portions of the catheter branches not coupled together.

Another embodiment of the present invention is described with respect to FIGS. 11-13. The embodiment of FIGS. 11-13 is similar to the embodiment of FIGS. 1-8 in that catheter 300 includes a first catheter branch 302 and a second catheter branch 304. First catheter branch 302 includes a first outer shaft 306, a first inner shaft 308, and a first balloon 310. A first inflation lumen 315 extends between first outer shaft 306 and first inner shaft 308, and is in communication with an interior of first balloon 310. A first guide wire lumen 316 extends through first inner shaft 308. Similarly, second catheter branch 304 includes a second outer shaft 318, a second inner shaft 320, and a second balloon 322. A second inflation lumen 325 extends between second outer shaft 318 and second inner shaft 320, and is in communication with an interior of second balloon 322. A first guide wire lumen 328 extends through second inner shaft 320.

A distal portion 309 of first inner shaft 308 includes a reduced neck portion 372, as shown in FIGS. 11-13. A moving pocket 360 is mounted around reduced neck portion 372. Moving pocket 360 includes a first portion 374 mounted around reduced neck portion 372 and a pocket portion 362 coupled to first portion 374. Pocket portion 362 is coupled to first portion 374 and is directed towards distal portion 321 of second inner shaft 320. First portion 374 may be an open cylinder with a proximal opening 368 and a distal opening 370. First portion 374 is sized and shaped such that it fits snugly around reduced neck portion 372, but it may slide along reduced neck portion 372 when a force is applied to moving pocket 360. Pocket portion 362 may be a closed cylinder with a proximal opening 364 and a distal wall 366.

In practice, a first guide wire 340 is inserted into a vessel. A proximal end of it first guide wire 340 is inserted into a distal opening 338 of first inner shaft 308. Distal portion 321 of second inner shaft is inserted into proximal opening 364 of pocket portion 362 such that first and second catheter branches 302, 304 are coupled to each other. Thus, by tracking first catheter branch 302 over first guide wire 340, both first and second catheter branches are tracked to the bifurcation site. Once at the bifurcation, force is delivered from second guide wire lumen 328 of second inner shaft 320 to move moving pocket distally along reduced neck portion 372 and thus freeing distal portion 321 of second inner shaft 320 from cup portion 362. The force delivered to move moving pocket 360 can be from a guide wire disposed within second guide wire lumen 328 or a force from a fluid injected through second guide wire lumen 328, for example, a saline solution.

Once first and second catheter branches 302, 304 are separated from each other, first and second catheter branches 302, 304 are advanced over first and second guide wires 340, 342 to the first and second branch vessels. First and second balloons 310, 322 are inflated by fluid delivered through first and second inflation lumens 315, 325. The balloons are then deflated and catheter 300 is removed from the vessel, as described above with respect to FIG. 4-8.

Figure 14:
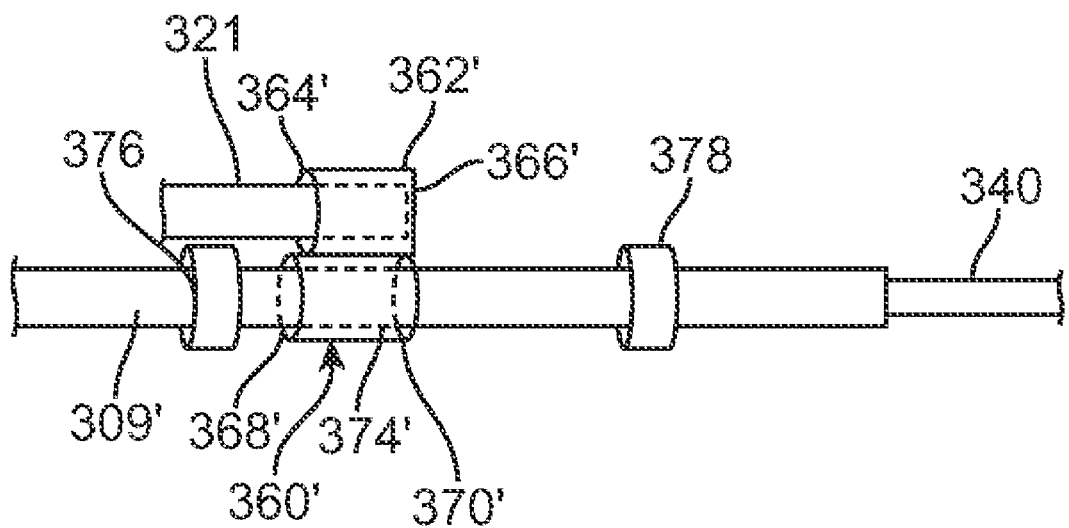
FIG. 14 illustrates a simplified, partial, elevational view of another embodiment of the distal portion of the catheter of FIG. 11, with the distal portions of the catheter branches coupled together.
Figure 15:
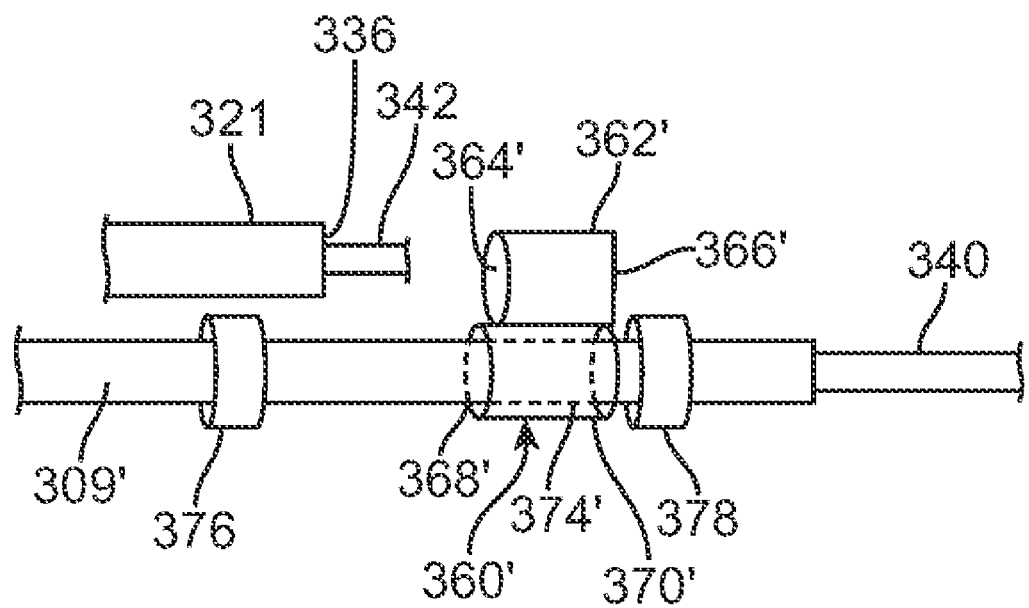
FIG. 15 illustrates a simplified, partial, elevational view of the distal portion of FIG. 14, with the distal portions of the catheter branches not coupled together.
Figure 16:
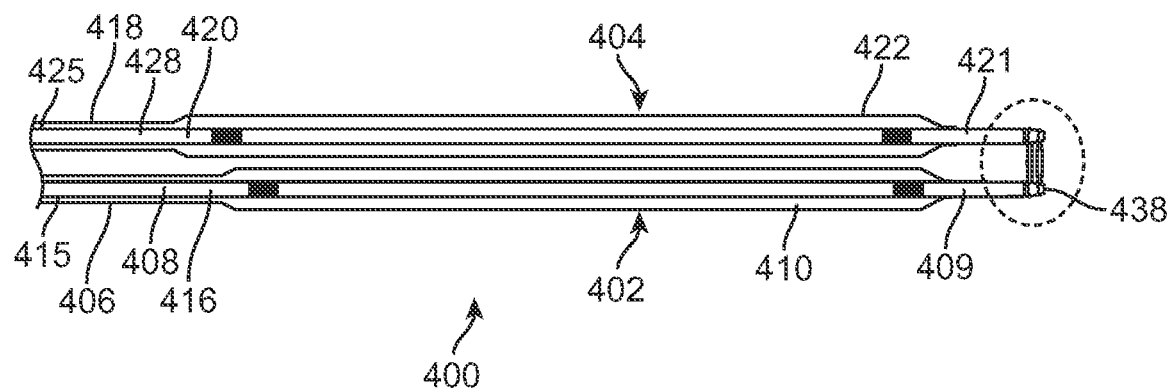
FIG. 16 illustrates a simplified, partial, elevational view of a bifurcated catheter in accordance with another embodiment of the present invention.

FIGS. 14 and 15 depict an alternative embodiment of the distal portion of catheter 300. In particular, distal portion 309' of the first inner shaft does not include a reduced neck portion as described with respect to FIGS. 11-13. Instead, moving pocket 360' is disposed over distal portion 309' and proximal and distal movement of moving pocket 360' is limited by a proximal stop 376 and a distal stop 378, respectively. In all other respects, the embodiment of FIGS. 14 and 15 functions in the same manner as the embodiment described with respect to FIGS. 11-13.

FIGS. 16-22 depict another embodiment of a bifurcated catheter 400 in accordance with the present invention. Catheter 400 includes a first catheter branch 402 and a second catheter branch 404. First catheter branch 402 includes a first outer shaft 406, a first inner shaft 408, and a first balloon 410. A first inflation lumen 415 extends between first outer shaft 406 and first inner shaft 408, and is in communication with an interior of first balloon 410. A first guide wire lumen 416 extends through first inner shaft 408. Similarly, second catheter branch 404 includes a second outer shaft 418, a second inner shaft 420, and a second balloon 422. A second inflation lumen 425 extends between second outer shaft 418 and second inner shaft 420, and is in communication with an interior of second balloon 422. A first guide wire lumen 428 extends through second inner shaft 420.

Figure 17:
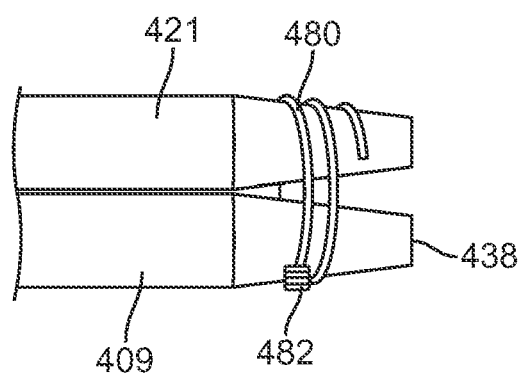
FIG. 17 illustrates a simplified, partial, elevational view of the distal portion of the catheter of FIG. 16.

A sheath 480 is coupled to a distal portion 409 of first inner shaft 408, as best seen in FIG. 17. Sheath 480 is coupled to distal portion 409 at a tack weld 482, but may be coupled by other means, such as adhesive bonding. Sheath 480 wraps around a distal portion 421 of second inner shaft 420 to couple distal portions 409, 421 together during delivery of catheter 400 to a bifurcation in a vessel.

Figure 18:
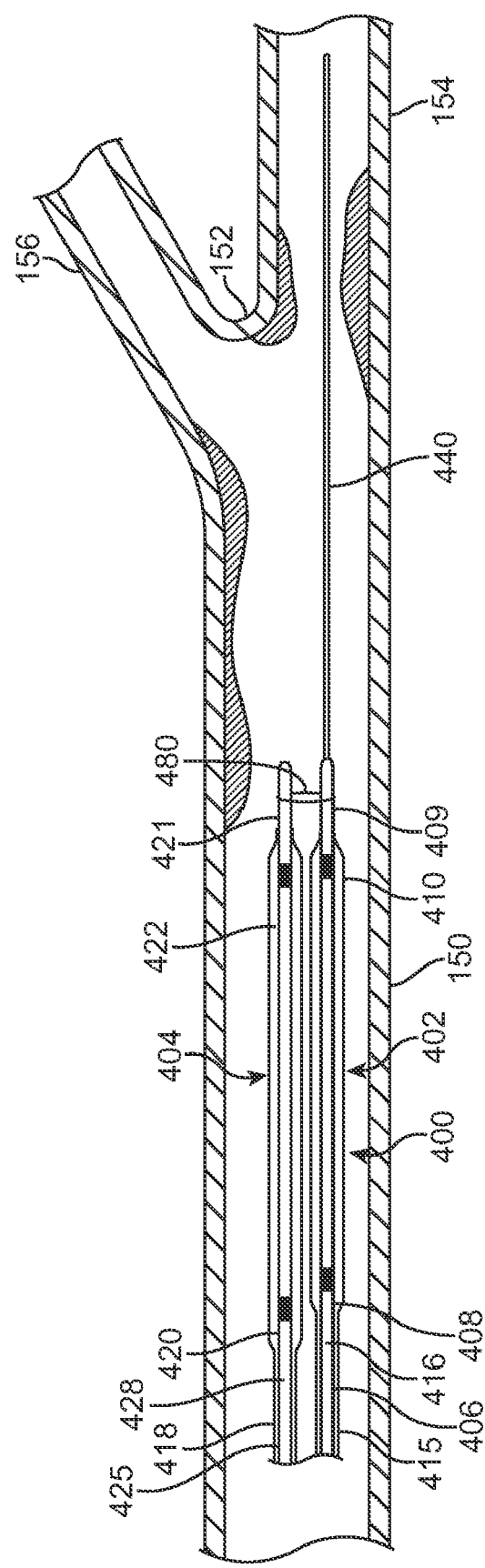
FIG. 18 illustrates the catheter of FIG. 16 in vivo, following the step of threading the catheter over a first guide wire.

FIGS. 18-22 illustrate a manner of practicing the invention utilizing catheter 400. First catheter branch 402 is threaded over a first guide wire 440 which is already in place in a vessel 150. More specifically, a proximal end of first guide wire 440 is threaded into a distal opening 438 of distal portion 409 of first inner shaft 408, and through first guide wire lumen 416. First catheter branch 402 is threaded over first guide wire 440 while sheath 480 is wrapped around distal portion 421 of second inner shaft 421, thereby coupling distal portions 409, 421 of first and second catheter branches 402, 404 together. Catheter 400 is thus threaded over first guide wire 440 and tracked to a position at or near bifurcation 152 of vessel 150, as illustrated in FIG. 18.

Figure 19:
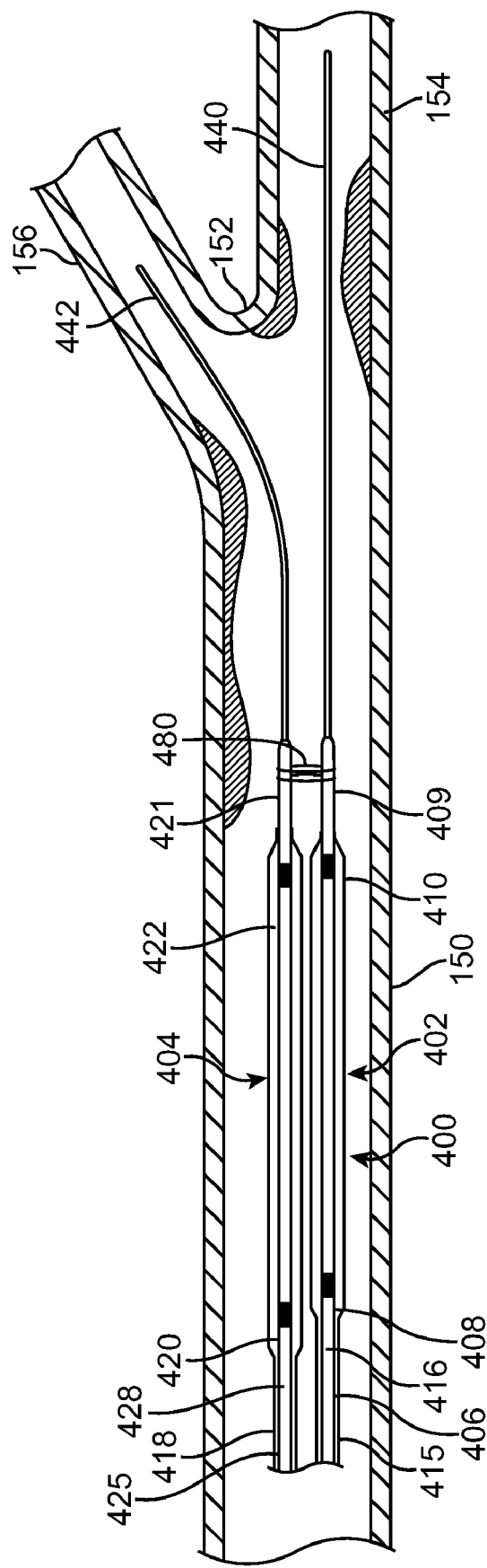
FIG. 19 illustrates the catheter of FIG. 16 after a second guide wire has been threaded through the second guide wire lumen and into the second branch vessel.

A second guide wire 442 may be pre-installed through second guide wire lumen 428 such that second guide wire 442 is advanced with catheter 400 as catheter 400 is advanced to the bifurcation site 152. Alternatively, second guide wire 442 may be inserted in second guide wire lumen 428 after catheter 400 is near the bifurcation 152. Once catheter 400 is near bifurcation 152, second guide wire 442 is advanced through a distal opening in distal portion 421 of second inner shaft 421 and into second branch vessel 156, as illustrated in FIG. 19.

Figure 20:
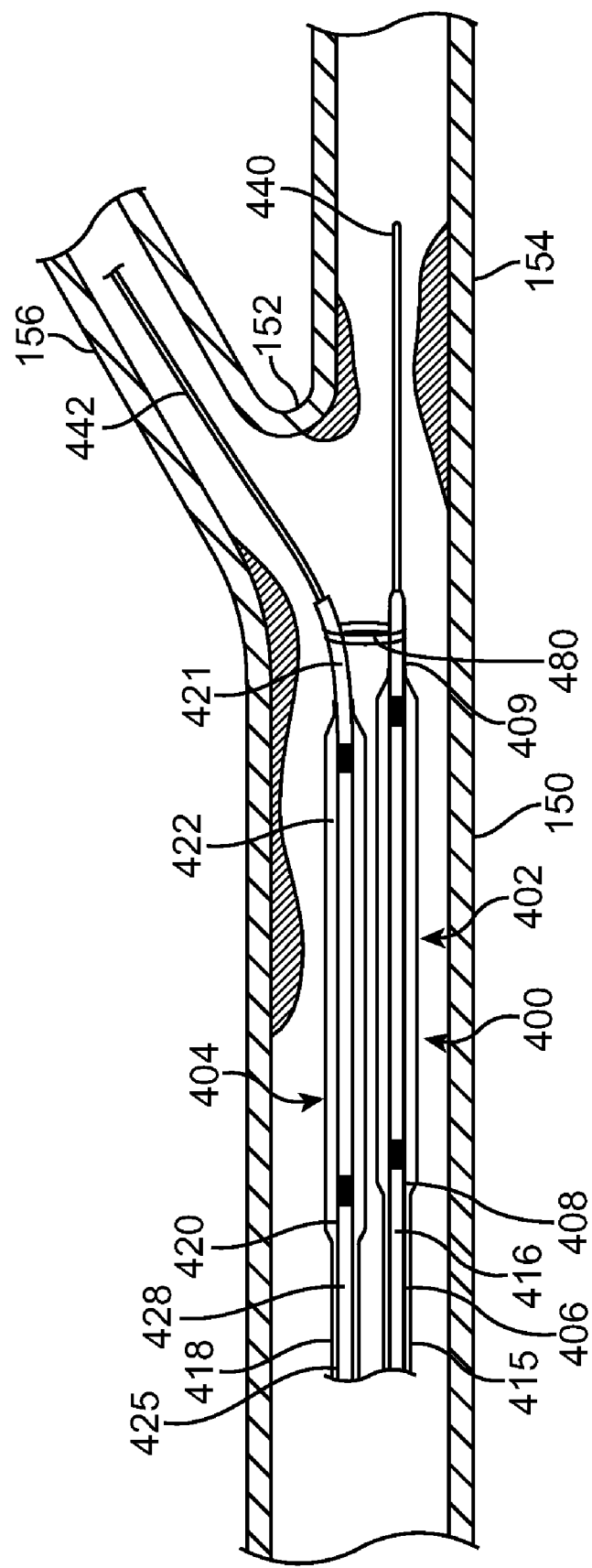
FIG. 20 illustrates the catheter of FIG. 16 as it approaches the bifurcation and the distal portions of the first and second catheter branches begin to separate.

Catheter 400 is then advance over guide wires 440, 442. As catheter 400 approaches bifurcation 152, first catheter branch 402, which is tracking over first guide wire 442, tracks towards first branch vessel 154. Meanwhile, second catheter branch 404, which is tracking over second guide wire 442, tracks towards second branch vessel 156. The divergent paths of first catheter branch 402 and second catheter branch 404 cause sheath 480 to unfold from distal portion 421 of second inner shaft 420, as illustrated in FIG. 20.

Figure 21:
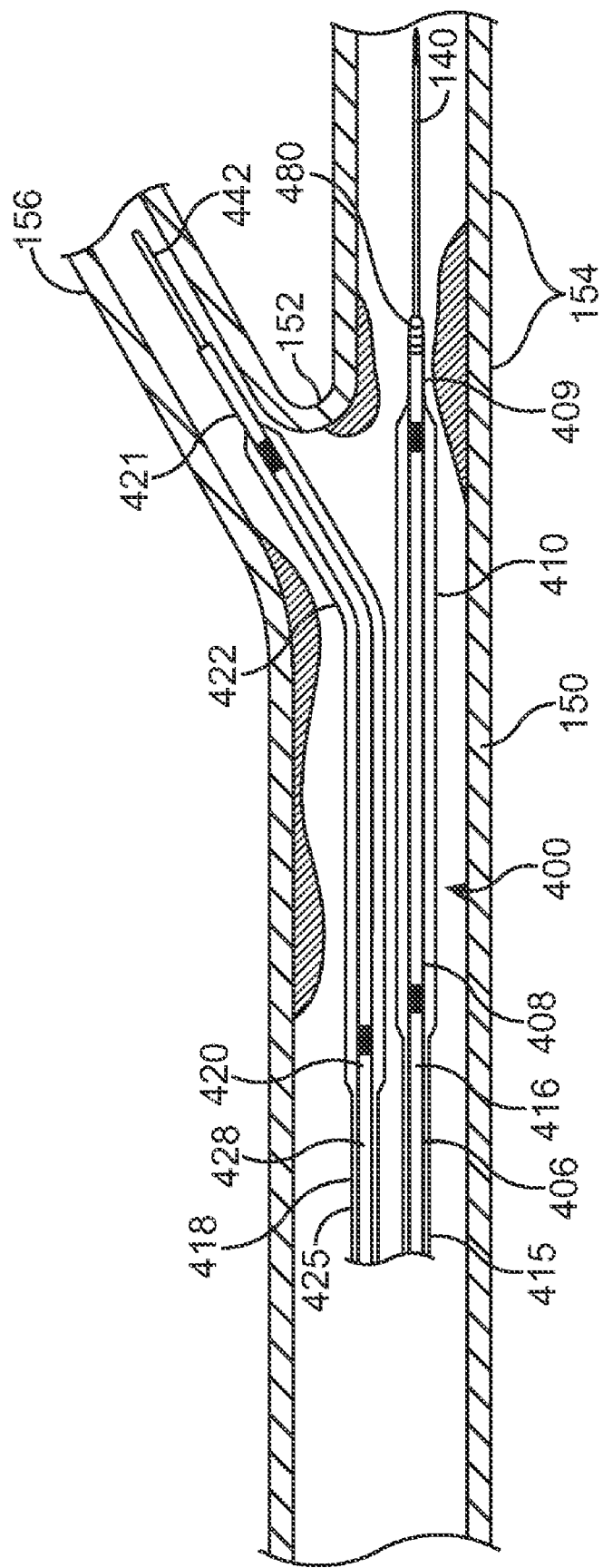
FIG. 21 illustrates the catheter FIG. 16 after the catheter branches have been advanced into the respective vessel branches such that the sheath coupling the catheter branches has been released and only surrounds the distal portion of the first catheter branch.

When first and second catheter branches 402, 404 are too far apart for sheath 480 to wrap around distal portion 421 of second inner shaft 420, sheath 480 releases distal portion 421 and wraps around distal portion 409 of first inner shaft 408, as illustrated in FIG. 21. With sheath 480 released from distal portion 421 of second inner shaft 420, first and second branches 402, 404 can then be positioned independently of one another such that first and second balloons 410, 422 may be positioned independently of each other. First and second catheter branches 402, 404 are advanced into first and second branch vessels 154, 156, respectively, as illustrated in FIG. 20.

Figure 22:
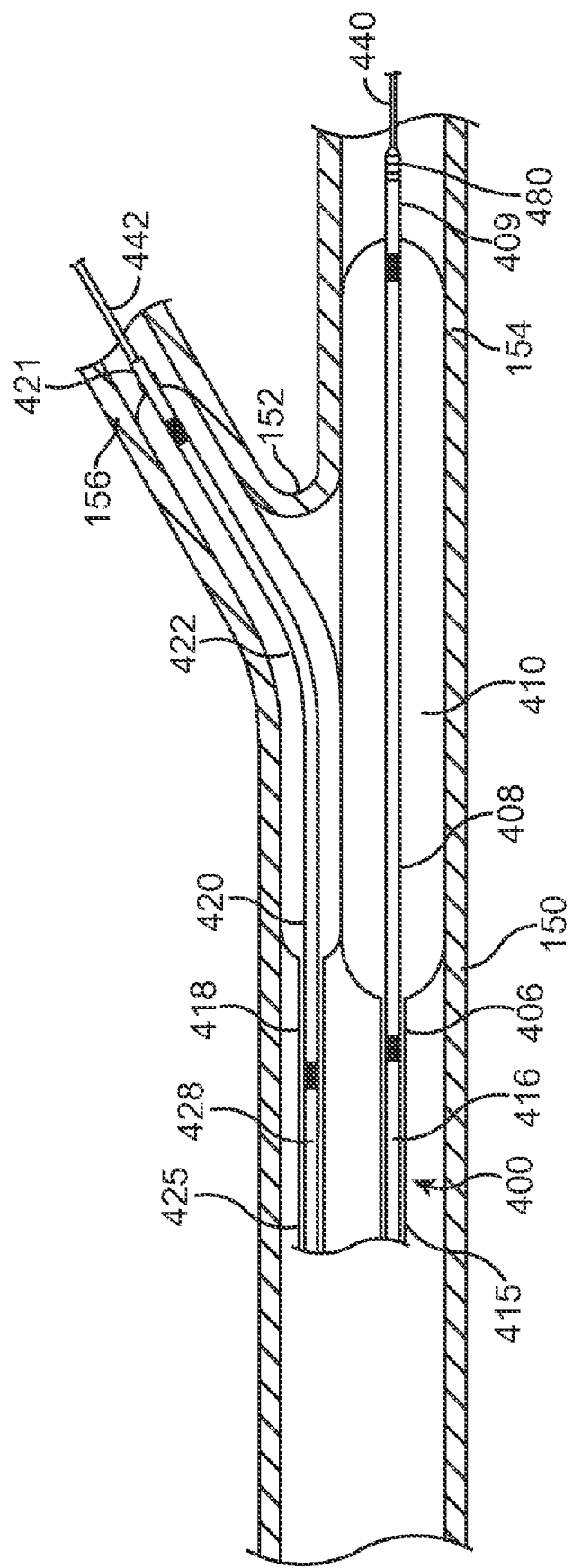
FIG. 22 illustrates the catheter of FIG. 16 subsequent to inflation of the balloon(s).

Once the entire assembly is properly positioned, pressurized fluid is supplied to first and second balloons 410, 422 through first and second inflation lumens 415, 425, as shown in FIG. 22. After first balloon 410 and second balloon 422 have been inflated as described above, first balloon 410 and second balloon 422 are deflated by draining the inflation fluid via first and second inflation lumens 415, 425. This allows the balloons to collapse in preparation for withdrawal of the assembly from vessel 150.

The various components of the catheters of this invention can be made of the same materials that are conventionally used for generally corresponding components of known catheters. Thus, for example, the various lumens can be made of materials such as polyethylene, polyethylene terephthalate, polyurethanes, polyesters, polyamides and copolymers thereof.

As another example, at least part of the outer or inner shafts may be stainless steel, polyimide or the like. A polyimide hypotube or similar material may encase the proximal shaft of the catheter. A sufficiently rigid material may prevent the twisting of the catheter and potential distortion of the lumens and guide wires within the catheter in the event a torque is applied to the catheter during positioning of the device.

The material of the balloons may be polyethylene, polyethylene terephthalate, nylon, polyamides, latex rubber, or other polymer. Guide wires can also be of any conventional construction and material, including solid or braided stainless steel. Hence, the term "wire" is used for these elements only as a matter of convenience, and that the material may not necessarily be wire.

The dimensions (e.g., the lengths, diameters, thicknesses, etc.) of various components of the catheters of this invention may be similar to the dimensions that are conventionally used for generally corresponding components of known catheters.

It would be understood by those of ordinary skill in the art that while the embodiments of the present invention discussed above are described with respect to a dual-lumen catheter including an outer shaft and an inner shaft, several different types of catheters known in the art could be used, for example, rapid exchange type catheters.

While various embodiments of the present invention have been described above, it should be understood that they have been presented by way of illustration and example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. An apparatus for treating a bifurcated region of a body lumen, comprising:
   a catheter having a first catheter branch and a second catheter branch, wherein the first catheter branch includes a first distal portion and the second catheter branch includes a second distal portion;
   a sheath coupled to the first distal portion and the second distal portion such that the first and second distal portions are coupled to each other.

2. The apparatus of claim 1, wherein the sheath is directly attached to the first distal portion and wrapped around the second distal portion.

3. The apparatus of claim 1, wherein the sheath is constructed such that it releases the second distal portion upon pulling the first and second distal portions apart, and upon the release, wraps around the first distal portion.

* * * * *